United States Patent [19]

Agnes et al.

[11] Patent Number: 4,795,595
[45] Date of Patent: Jan. 3, 1989

[54] TAURINE DERIVATIVES

[75] Inventors: Giovanni Agnes; Maria Altamura, both of Novara, Italy

[73] Assignee: Farmitalia Carlo Erba S.p.A., Milano, Italy

[21] Appl. No.: 77,238

[22] Filed: Jul. 24, 1987

[30] Foreign Application Priority Data

Jul. 31, 1986 [GB] United Kingdom ............ 8618765

[51] Int. Cl.$^4$ ............... C07C 143/56; C07C 143/64; C07C 143/02
[52] U.S. Cl. .............................. 260/508; 260/509; 260/510; 260/513 N; 548/491
[58] Field of Search ............... 260/513 N, 508, 509, 260/510; 548/591

[56] References Cited

FOREIGN PATENT DOCUMENTS 1954090  5/1971  Fed. Rep. of Germany ... 260/513 N
85066952 9/1983  Japan .

OTHER PUBLICATIONS

Gilbert Sulfonation and Related Reactions (1965) pp. 220–222.
J. Agr. Food Chem., 1984, 32, 992–996.

Primary Examiner—Alan Siegel
Attorney, Agent, or Firm—Oblon, Fisher, Spivak, McClelland & Maier

[57] ABSTRACT

A process of preparing taurine-containing peptides of formula (I):

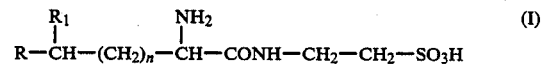

comprises reacting a protected aminoacid with cysteamine or cystamine in the presence of a condensing agent, oxidizing the resulting compound and deprotection.

3 Claims, No Drawings

TAURINE DERIVATIVES

DESCRIPTION

The invention relates to a process for the preparation of taurine-containing peptides of formula (I):

(I)

wherein
R is a hydrogen atom or $C_1$–$C_6$ alkyl, phenyl, p-hydroxyphenyl or 1H-indol-3-yl group;
$R_1$ is a hydrogen atom, an amino group or a $C_1$–$C_6$ alkyl group; and
n is 0 or an integer from 1 to 6; and
the pharmaceutically acceptable salt thereof.

Taurine containing peptides and. the pharmaceutically acceptable salt thereof are endowed with a salty taste, and can be used as an artificial seasoning for food as described in the Japanese published application No. 85066952.

BACKGROUND ART

Although synthetic methods for the preparation of peptides by the coupling of protected and activated aminoacids are well known, they generally fail when applied to the synthesis of taurine-containing peptides. A recent paper reports the preparation of dipeptides containing taurine (J. Agr. Food. Chem., 1984, 32, 992–996): a protected and activated amino-acid compound such as benzoyloxycarbonyl-aminoacid succinimide ester and 2-aminoethanesulphonic acid (taurine) were coupled and deprotected to yield the expected taurine derivative. The procedure has critical disadvantages such as:

1. the high cost of the hydroxysuccinimide used to activate the amino acid;
2. the difficulty of recovering the final compound; and
3. exhaustive extractions with organic solvents required.

and so is not suitable for industrial operation on a large scale.

THE INVENTION

The invention provides a process of preparing taurine-containing peptides which comprises condensing a protected aminoacid with cysteamine or cystamine in the presence of a condensing agent, oxidizing the resultant compound and removing the protecting groups. This can be represented by the following scheme:

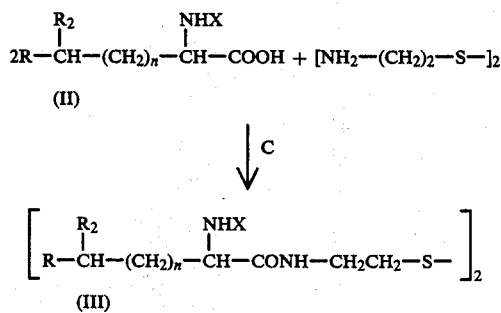

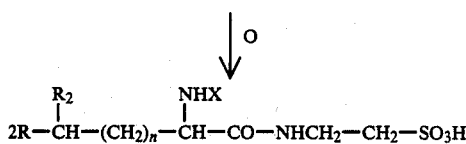

wherein
X is a protecting group for a terminal nitrogen atom, for example of aromatic urethane or aralkyl or acyl type; and
n, R and $R_1$ have the above meanings;
$R_2$ is a hydrogen atom, or a $C_1$–$C_6$ alkyl, or a group of the formula NHX wherein X has the meanings above specified;
C is a condensing agent;
O is an oxidizing agent; and
D is a deprotecting agent.

Preferred terminal nitrogen atom protecting groups include (of the aromatic urethane type) benzyloxycarbonyl, 2,4-dichlorobenzyloxycarbonyl, 2-bromobenzyloxycarbonyl and 4-methoxybenzyloxycarbonyl groups; (of aralkyl type) benzyl, benzhydryl and trityl groups; and (of acyl type) formyl, acetyl, propionyl, benzoyl, 4-nitrobenzoyl groups.

Preferred condensing agents C include methyl chloroformate, ethyl chloroformate, propyl chloroformate, phenyl chloroformate or an association thereof with an aliphatic or heterocyclic or heteroaromatic tertiary amine such as trimethylamine, triethylamine, NN'-diethyl-aniline or N-methyl-morpholine.

Preferred oxidizing agents O include bromine, chlorine organic or aliphatic acyl hydroperoxides or mixtures of hydrogen peroxide ($H_2O_2$) or an organic acid such as formic or acetic.

Preferred deprotecting agents D are mineral acids such as sulphuric, nitric, hydrochloric, hydrobromic, hydroiodic, phosphoric, or perchloric acid; or organic acids such as formic, acetic, trifluoroacetic, or chloroacetic acid; or molecular hydrogen or a hydrogen donor associated with a Group VII metal catalyst, depending on the type of protecting group to be removed.

n is preferably 0,1,2 or 3;
R is preferably a hydrogen atom, or a methyl or ethyl group; and
$R_1$ is preferably a hydrogen atom, or a methyl or amino group.

The preferred dipeptides of formula I prepared according to the invention are:
H-Val-Tau(I, n=0, R=$R_1$=$CH_3$);
H-Orn-Tau(I, n=2, R=H, $R_1$=$NH_2$);
H-Lis-Tau(I, n=3, R=H, $R_1$=$NH_2$)
H-$A_2$pr-Tau(I, n=0, R=H, $R_1$=$NH_2$); and
H-$A_2$bu-Tau(I, n=1, R=H, $R_1$=$NH_2$).

The pharmaceutically acceptable addition salts of the dipeptides prepared according to the invention can be derived in a conventional manner from a variety of inorganic and organic acids such as sulphuric, phosphoric, hydrochloric, hydrobromic, hydroiodic, nitric, sulphamic, citric, lactic, pyruvic, oxalic, maleic, succinic, tartaric, cinnamic, acetic, trifluoroacetic, benzoic, salicylic, gluconic, or ascorbic.

The protecting groups and the condensing agent C are preferably selected so as to avoid the risk of racemization. The symbols and abbreviations used herein for amino acids and peptides are those recommended by IUPAC, see Eur. J. Biochem. 138, 9-37 (1984). Moreover, Taurine (Tau) means a 2-aminoethan-sulphonic acid residue.

The individual steps in the process of the invention can be described in more detail as follows:

A protected amino acid (II) is dissolved in the minimum amount of an organic solvent such as an ether, cyclic ether, ketone, nitrile, amide, sulphoxide, hydrocarbon, or halocarbon. An equivalent amount of an alkyl chloroformate of the general formula $R_3OCOCl$, wherein $R_3$ is an alkyl or aryl residue of up to 8 carbon atoms, and of a base such as tertiary amine, preferably as defined above under C is added.

Cystamine is then introduced. Cysteamine transforms spontaneously into cystamine through air oxidation, and so can be used instead of cystamine. All the above operations are performed in a stirred flask, at between $-30°$ C. and room temperature. The reaction is better run under an inert gas atmosphere. The product (III) of the reaction can be recovered from the crude mixture by conventional methods, such as filtration or decantation. Separation of the product (III) can be better obtained by dilution of the reaction mixture with an aliphatic ether or an aliphatic or aromatic hydrocarbon. Optionally the reaction solvent can be recovered by distillation and the crude residue can be suspended in cold water and filtered.

The product (III) is oxidized to (IV) by mixing the product (III) with a solution of an oxidizing agent. The reagent of choice is commercially available hydrogen peroxide ($H_2O_2$ content from 10 to 70%) dissolved in formic or acetic acid. Optionally, preformed organic peroxyacids such as peroxyformic, peroxyacetic, peroxybenzoic, metachloroperbenzoic, or perphthalic acid can be used. Alternatively chlorine, bromine, iodine or a mixture of two or more thereof can be used as the oxidizing agent. The oxidation is run at from the freezing point of the mixture to $+20°$ C. The reaction time is generally less than 5 hours. The excess of the oxidizing agent is then eliminated by addition of a reducing agent such as dimethylsulphide, sodium bisulphite, sodium dithionite or by addition of a finely divided (noble) Group VIII metal (preferably palladium or platinum) alone or in a supported form. This reaction is run at room temperature. The resulting mixture is filtered and the volatile components are eliminated by vacuum distillation. The crude residue is used for the following step.

The crude protected dipeptide containing taurine (IV) is shaken with a solution of a mineral or organic acid dissolved in a solvent for example an aliphatic or cyclic ether, ketone, or ester. The mixture is then filtered, and the residue dried "in vacuo" to give the product (I). The last reaction is run at from $-30°$ C. to $+30°$ C. Alternatively, the deprotection can be performed by molecular hydrogen or a hydrogen donor by shaking the solution of (IV) in acetic acid under a hydrogen atomsphere in a presence of a Group VIII metal catalyst alone or in supported form. Palladium or platinum on carbon are preferred for this purpose. The pressure of hydrogen may be from 1 to 10 atmospheres; the temperature from $-30°$ C. to $+50°$ C. The reaction time is generally shorter than 2 hours but may be up to five hours.

EXAMPLE 1

L-ornithyltaurine hydrochloride

Method A

N,N-dibenzyloxycarbonylornithine (10 g-25 mmol) was dissolved in THF (50 ml) and N-methylmorpholine (2.8 ml). Methyl chloroformate (2 ml) was added at $-5°$ C. under a nitrogen atmosphere. After stirring at the same temperature for 15 min., a solution of cystamine dihydrochloride (2.9 g-13 mmol) and triethylamine (3.6 ml-26 mmol) in 50 ml water was added at $-5°/+5°$ C. After standing at 5° C. for 30 min., and at room temperature overnight, the reaction mixture was filtered. The residue was washed on the filter with water and diethyl ether, to give IIIa ($X=COOCH_2Ph$, $R_2=NHCOOCH_2Ph$, $R=H$, $n=3$) as a white solid (11.4 g-(100%)-m.p. 159°-61° C.). 10 ml 30% $H_2O_2$ were added to 100 ml HCOOH 98%, and the solution stirred at room temperature for one hour.

Disulfide IIIa (7 g-7.6 mmol), as obtained in the previous step, was added at 0° C., and the mixture stirred at room temperature for 5 hours. The excess oxidant was destroyed by addition of dimethylsulphide or 10% palladium on charcoal. The filtered solution was evaporated in vacuo to give crude N,N'-dibenzyloxycarbonylornithyltaurine IV a ($X=COOCH_2Ph$, $R_2=NHCOOCH_2Ph$, $R=H$, $n=3$).

The protecting group was removed by hydrogenolysis under hydrogen (atmospheric pressure) at room temperature in the presence of Pd 5% palladium on charcoal. After 1-2 h, the catalyst was removed by filtration and the filtrate evaporated in vacuo. The crude product was crystallized from methanol. L-ornithyltaurine hydrochloride was finally obtained by addition of a solution of hydrogen chloride in dioxan, and filtration under nitrogen atmosphere. The crystalline hygroscopic powder was washed with diethyl ether and dried in vacuo. Yield: 65% from IIa. $(\alpha)_D^{20°}=+6°$ (c=1, $H_2O$).

Method B

N,N-di-t-butyloxycarbonylornithine was condensed with cystamine as described in Method A above. At the end of the reaction, THF was removed by distillation in vacuo and the residue was dissolved in a solvent mixture ($CH_2Cl_2/CH_3OH$ 95:5). The organic phase was washed in sequence with water, HCl dil. aq., $NaHCO_3$ 5% aq., and water, and finally dired over $Na_2SO_4$. Evaporation in vacuo and crystallization from diethyl ether gave IIIb ($X=COOC(CH_3)_3$; $R_2=NH-COOC(CH_3)_3$; $R=H$; $n=3$) as a crystalline solid (yield: 85%). Crude IIIb was oxidized as described in Method A for IIIa, and the protecting group was removed by HCl/dioxane to give crystalline L-ornithyltaurine hydrochloride in a yield of 85% (from IIIb).

EXAMPLE 2

L-valyltaurine

N-formyl-L-valine (2 g-13.7 mmol) was dissolved in THF (30 ml) and N-methylmorpholine (1.5 ml). Methyl chloroformate (1.1 ml) was added at $-5°$ C., under $N_2$ atmosphere, and the mixture stirred at the same temperature for 15 min. A solution of cystamine dihydrochloride (1.55 g) and triethylamine (2 ml) in 30 ml water was added at 0°–10° C. The mixture was stirred at 0° C. for 30 min and at room temperature overnight. The solvent was evaporated off in vacuo, and the crystalline residue filtered and washed several times with water and diethyl ether. Yield: 2.1 g (75%) of IIc (X=CHO, R=R$_2$=CH$_3$; n=0)-Crude IIc was oxidized as described in the Example 1 (method A), and the formyl protecting group removed by hydrogen chloride in dioxan, giving L-valyl-taurine as a crystalline solid (yield: 1.2 g (81%).

We claim:

1. A process for preparing taurine containing peptides of formula I:

where R is a hydrogen atom, a C$_1$–C$_6$ alkyl, phenyl p-hydroxyphenyl or 1-H-indol-3-yl group; R$_1$ is a hydrogen atom, an amino group or a C$_1$–C$_6$ alkyl group; n is 0 or an integer from 1 to 6 and their pharmaceutically acceptable addition salts, which process comprises reacting an N-protected amino acid of the general formula II:

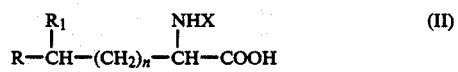

wherein R, R$_1$ have the meanings given above, X is an aromatic urethane, aralkyl or acyl protecting group which also protects the amino group when R$_1$ is amino, dissolved in tetrahydrofuran, at a temperature of between −30° C. and room temperature under an inert gas atmosphere, with an alkyl or aryl chloroformate in the presence of a tertiary amine, to form a mixed anhydride of the protected amino acid, condensing said mixed anhydride with an aqueous solution of cystamine, at a temperature of from −30° C. to room temperature to obtain a condensation product, oxidizing the disulfide bond of the condensation product to sulfonic groups by means of hydrogen peroxide, an organic peroxyacid, chlorine or bromine or a mixture of two or more thereof in formic or acetic acid at a temperature of from the freezing point of the mixture to 20° C., and removing the protecting group or groups by hydrogenolysis under hydrogen, at a pressure of from 1 to 10 atmospheres in the presence of a Group VIII metal catalyst at a temperature of from −30° C. to 50° C., or by treatment with a mineral acid at a temperature of from −30° C. to 30° C., to obtain the desired peptides of formula I.

2. A process according to claim 1 in which the condensing agent has the formula R$_3$OCOCl, wherein R$_3$ is an alkyl or aryl residue of up to 8 carbon atoms.

3. A process according to claim 1, wherein said tertiary amine is N-methylmorpholine.

* * * * *